United States Patent [19]

King

[11] 4,352,360
[45] Oct. 5, 1982

[54] SEMICONDUCTOR LOW-THRESHHOLD ELECTRODE

[75] Inventor: Wendell L. King, North Oaks, Minn.

[73] Assignee: Medtronic, Inc., Minneapolis, Minn.

[21] Appl. No.: 248,766

[22] Filed: Mar. 30, 1981

[51] Int. Cl.³ .............................................. A61N 1/04
[52] U.S. Cl. ................................. 128/786; 128/419 P
[58] Field of Search ............................... 128/784–786, 128/419 P, 798, 783, 802, 803, 442

[56] References Cited

U.S. PATENT DOCUMENTS

| 3,533,403 | 10/1970 | Woodson | 128/642 |
| 3,994,302 | 11/1976 | Brennen | 128/784 |
| 4,281,668 | 8/1981 | Richter et al. | 128/784 |

FOREIGN PATENT DOCUMENTS

| 2144902 | 6/1973 | Fed. Rep. of Germany | 128/786 |
| 2842318 | 9/1978 | Fed. Rep. of Germany | |

OTHER PUBLICATIONS

Non-Polarizable Vitreous Carbon Pacing Electrodes in Animal Experiments, by Richter, Weidlich, Sturm, David, Brandt, Elmqvist and Thoren, "The Structure of Polymers", Section 13—Electrical Properties, Conductance in Polymers, pp. 671–683.

Primary Examiner—Lee S. Cohen
Attorney, Agent, or Firm—John L. Rooney; Joseph F. Breimayer; Robert C. Beck

[57] ABSTRACT

An electrode for a body implantable lead having a semiconductor surface for the coupling of electrical signals to the body tissue. A first approach uses several materials of differing conductivities. These materials are arranged in layers such that the material having the lowest conductivity is in direct contact with body tissue. The layers are then added in increasing order of conductivity. The intersection of two materials may be abrupt or may be a smooth transition fashioned by a combination of the two materials. The second approach provides an abrupt transition from the highly conductive materials within the lead body to a semiconductor material having direct exposure to the body tissue. The conductor within the body implantable lead is preferably fabricated using drawn brazed strand coils arranged in multifilar fashion. The conductor coils are insulated using a polyurethane sheath.

10 Claims, 7 Drawing Figures

SEMICONDUCTOR LOW-THRESHHOLD ELECTRODE

BACKGROUND OF THE INVENTION

1. Field of the Invention

The present invention relates generally to implantable medical devices and more specifically relates to body implantable electrodes.

2. Description of the Prior Art

By far the majority of body implantable leads in use, particularly in the pacing field, utilize metallic electrodes. A favored material for such metallic electrodes is platinum or a platinum alloy. Other materials which have been used include stainless steel, titanium and so forth. Care must be exercised in chosing these materials to assure that they are biocompatible and capable of long-term chronic implantation. For that reason, materials in the platinum group have been preferred notwithstanding their relatively high cost.

The use of other than solid metallic electrodes has been relatively rare. Lagergren in U.S. Pat. No. 3,911,928 teaches an electrode surface alternately covered with highly conducting metallic materials and insulating materials. These materials are arranged in the fashion of a mesh. It is expressed by Lagergren that such an arrangement is desirable as it provides a large contact surface for sensing purposes and yet presents a relatively small contact surface for stimulating purposes thereby producing sufficiently large charged densities.

Other persons have taught the use of materials which are not highly conducting metals. By far the most often preferred non-metallic material is carbon. Thorén in U.S. Pat. No. 4,149,542 teaches an endocardial electrode having a carbon tip. The purpose of using the carbon tip is stated as providing a heart tissue compatible conductive material. The concern herein is the growth of fibrotic tissue and therefore, carbon is chosen because it is thought to be highly biocompatible. However, Thoren teaches no selection of material based upon its conductivity.

Richter, in Offenlegungschrift No. 28 42 318 teaches an implantable carbon electrode. Again, the concern is that of body compatibility. Richter teaches that metal stimulation electrodes are less desirable because they cause slow degeneration of the tissue adjoining the electrodes. Therefore, it is felt that a carbon tip electrode, because it is more biocompatible, will provide a lower overall chronic energy threshhold.

SUMMARY OF THE INVENTION

The present invention uses a biocompatible material in contact with the surface of the body tissue as taught in the prior art. But, in addition it uses a semiconductor material having conductivities substantially lower than those of metals for the express purpose of providing an improved impedance match between the electrode and the body tissue. Certain materials are particularly desirable to this end because they exhibit charge transfer characteristic similar to those found within the body cells. In the preferred mode of practising the present invention certain semiconductive polymer materials are preferred.

A body implantable lead constructed in accordance with the present invention has such a semiconductor material in direct contact with the body tissue to be stimulated. The main body of the body implantable lead has a conductor system having less resistivity and high flex strength. The low resistivity conductor system may be coupled directly to the semiconductor materials in contact with the body tissue or a graded semiconductor electrode technique may be employed. In this approach, several different semiconductor materials are used having different conductivities. The low resistivity conductor system is coupled to the semiconductor material having the next highest conductivity which, in turn, is coupled to the semiconductor material having the next highest conductivity and so forth. In this fashion, an electrode is created having a high conductivity at its proximal end and a much lower conductivity approaching that of the body tissue to be stimulated at its distal end. The graded conductor electrode will yield leads with very low polarization effects.

DETAILED DESCRIPTION OF THE PREFERRED EMBODIMENTS

The present invention is described in terms of a unipolar implantable cardiac pacing lead having a semiconductor electrode at its distal tip. Those of ordinary skill in the art will be able to apply the invention disclosed herein to other body implantable leads. Furthermore, the disclosure contained herein describes numerous materials which are preferable in constructing the semiconductor electrode. However, those of ordinary skill in the art will be readily able to apply these teachings to other similar materials. Of most importance is that the resistivity of materials used is substantially higher than is found in the metallic prior art electrodes or even the prior art carbon electrodes.

Figure 1:
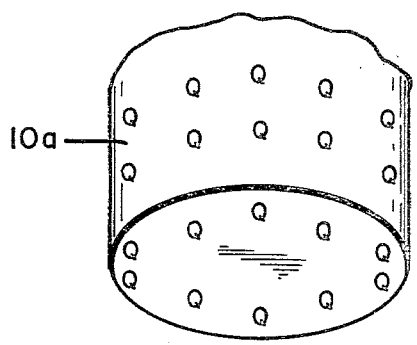
FIG. 1 is a schematic representation of the conductivity of charge in a highly conductive prior art electrode of metallic or carbon material.

FIG. 1 is a schematic representation of the charge distribution within a prior art metallic or carbon distal electrode. Notice that the charge is uniformly distributed on the surface of the material. This is, of course, a characteristic of metals and other highly conductive materials. Conduction in this situation occurs primarily through the transfer of electrons. It is felt that the use of highly conductive electrodes is a natural inclination in designing a body implantable lead since it minimizes the resistance to the transmission of a stimulation pulse from a remotely located pulse generator to the body tissue to be stimulated. However, it has been noted that body implantable lead systems having extremely low resistivities tend to supply more current than is actually required for stimulation which leads to premature depletion of the implantable energy source. As herein considered a conductor is defined as having a resistivity of between $10^0$ and $10^4$ microhm cm.

Figure 2:
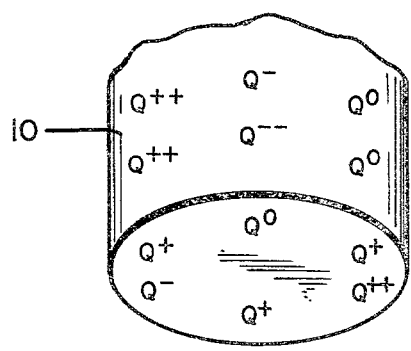
FIG. 2 is a corresponding schematic of the heterogenous charge distribution of the semiconductor electrode employed in the present invention.

FIG. 2 is a corresponding schematic representation of a distal electrode of semiconductor material. As used herein semiconductors are considered to have electrical resistivities in the range $10^4$ to $10^{10}$ microhm cm. It should be noted that in most such semiconductor materials as shown schematically, the charge density of transmission is heterogenous. Also characteristic of a many semiconductor materials is that the transfer of charge—that is to say, the current flow within the semiconductor—is via the transfer of ions rather than the transfer of free electrons as in the case of the conductors.

Figure 3:
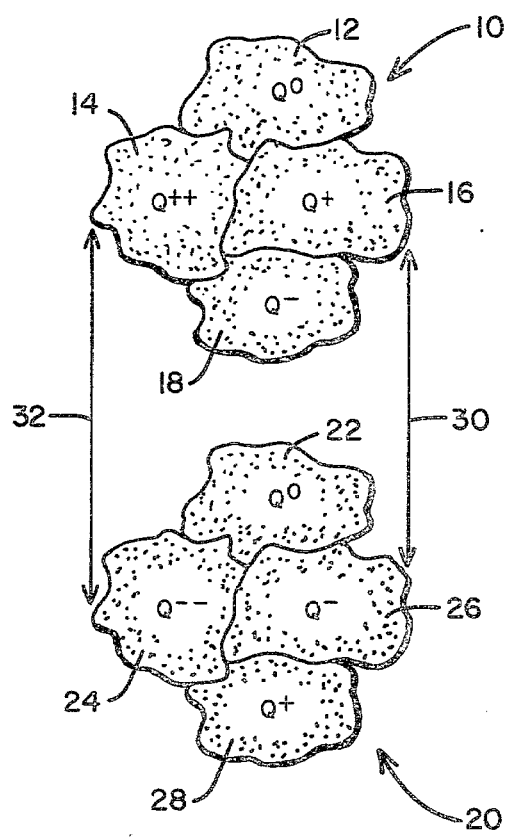
FIG. 3 is a schematic representation of the matching of the heterogenous charge transmission from the semiconductor electrode of the present invention to a small segment of body tissue.

FIG. 3 is a schematic representation of a very small piece of a semiconductor electrode 10 as contacting a very small cross-section of body implantable tissue 20. During operation, the cross-section of body implantable electrode 10 would be physically adjacent and touching the body tissue 20. For the purposes of illustration, the two surfaces have been displaced as shown along lines 30 and 32. For the purposes of this illustration the resistivities of body implantable electrode 10 and body tissue 20 are assumed to be substantially equivalent being in the range of $10^4$ to $10^{10}$ microhm cm.

Because of the close impedance match involved and because both the semiconductor electrode 10 and the body tissue 20 are semiconductors with relatively few free electrons but primarily conducting via ion flow, you will see that the charge on the surface of body implantable semiconductor electrode 10 matches the charge on the surface of body tissue 20. As can be visualized from the figure, body tissue 20 is composed of individual cells 22, 24, 26 and 28. These cells are, of course, separate physical entities within the body tissues. As is known of the physiology, each of the cells will have a slightly different electrochemical constituency at any point in time and therefore each of the cells will have a different stimulation threshhold. To properly minimize the total energy threshhold of the system, it is desirable to stimulate each of the cells at any one given point in time with only so much energy as is required by its specific charge requirement at the instant of stimulation. As is schematically represented in FIG. 3, this is effectively accomplished by using a semiconductor material in contact with the body tissue having an impedance essentially equivalent to that of the body tissue to be stimulated.

Figure 4:
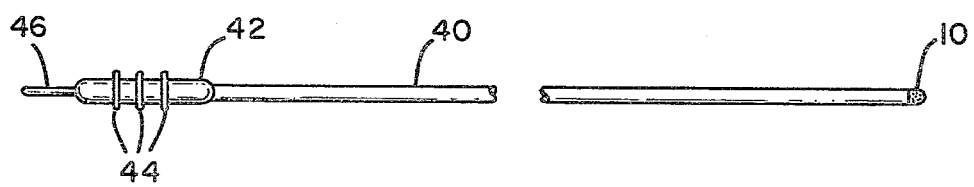
FIG. 4 is a plan view of a lead employing the present invention.

FIG. 4 is a plan view of a unipolar body implantable lead employing a semiconductor electrode. The distal end of the body implantable lead has a semiconductor electrode 10 as shown. The main body of the body implantable lead 40 is covered by an insulating sheath 42 of body inert material such as urethane or silicone rubber. The distal end of the body implantable lead has an electrical connector having sealing rings 44 and an electrical conducting terminal pin 46. Not shown in FIG. 4 is the conductor which electrically couples semiconductor electrode 10 to conducting terminal pin 46. This conductor is preferably of a low resistivity material such as a drawn brazed strand configuration using MP35N wire having a silver matrix. The wire is preferably arranged as a space wound coil in multifilar fashion.

Figure 5:
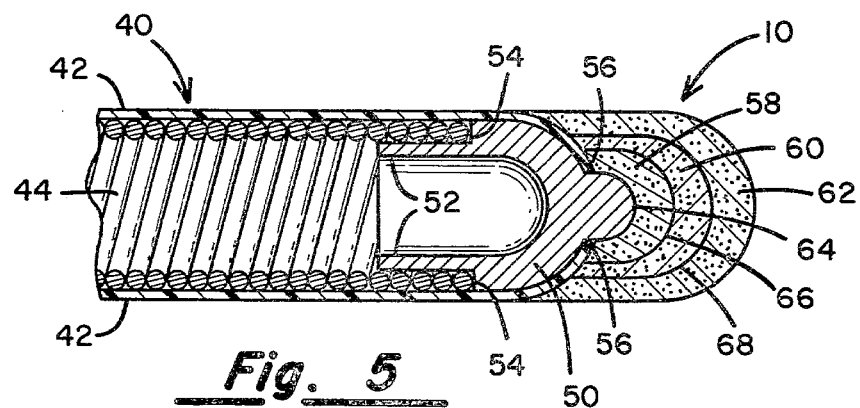
FIG. 5 is a cross-sectional view of a graded semiconductor electrode.

FIG. 5 is a cross-sectional view of one embodiment of semiconductor electrode 10. The space wound conductor coil 44 is shown as being insulated from contact with body tissue by insulating sheath 42. At the distal tip of conductor coil 44 is located the highly conductive element 50. Element 50 is preferably fabricated from platinum or other body compatible metal having a low resistivity. The resistivity of element 50 should be less than $10^2$ microhm cm. Other materials such as titanium which have a slightly higher resistivity may be used. It is important, however, that element 50 be of a highly conducting metal to provide a low impedance coupling to conductor coil 40 and to supply structural strength for the semiconductor electrode 10.

Element 50 is attached to conductor coil 44 by welds as shown at point 54. Notice that element 50 also has trailing appendages 52 which enable additional welding to other coils of the multifilar conductor coil 44.

Element 58 which is electrically coupled directly to element 50 has a resistivity greater than that of element 50. That is, the resistivity of element 58 is preferably in the range of $10^2$ to $10^5$ microhm cm. A preferred material for this purpose is polypyromelitimide. This substance has a resistivity in the range of 500 microhm cm. An alternative material to be used for element 58 is a material such as carbon having a resistivity of $4(10^3)$ microhm cm. Element 58 is bonded to element 50 creating the junction 64 through which the current will flow. The bonding technique to be employed depends on the material but molding or adhesive techniques may be employed. The important thing is to allow a sufficiently large surface for junction 64 for the direct conductivity between elements 50 and 58.

Element 60 is of a material having a higher resistivity than element 58. It should have a resistivity in the range of approximately $10^5$ to $10^8$ microhm cm. A preferred material for element 60 is polypentacene which has a resistivity of about $10^8$ microhm cm. Again, element 60 may be bonded to element 58 using any known convenient means, however care must be exercised to allow most of the surface area of junction 66 to be the direct junction of the material in element 58 with the material in element 60. For that reason, molding is the preferred form of manufacture.

Element 62 has direct contact with the body tissue. Therefore, it should have a conductivity approximating that of the body tissue to be stimulated. A preferred material for element 62 is polypyrene, having a resistivity of about $10^9$ microhm cm. It will be noticed that element 62 which is in contact with the body must be body compatible and the preferred materials, with the exception of element 50, are all polymers. An excellent text on the structure and conductivity of other polymers to be used to practice the present invention may be found in the text *The Structure of Polymers*, by M. C. Miller, Reinhold Publishing Corporation, 1966. The text provides a discussion at pages 671-675 of conductance in polymers, and at pages 675-683 discusses the use of polymers as semiconducting materials in combination with metallic elements.

Figure 6:
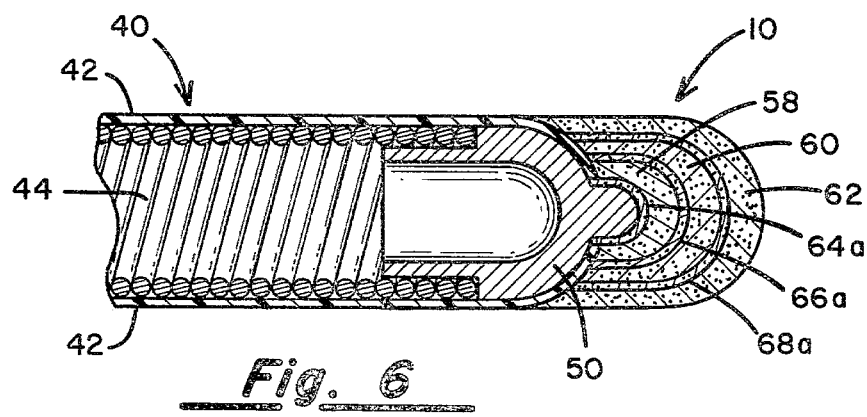
FIG. 6 is a cross-sectional view of a graded semiconductor electrode having transition zones.

FIG. 6 shows an alternate embodiment of the semiconductor electrode 10. Notice that, in the embodiment of FIG. 6, the same structure and materials are used as was disclosed in relationship to the embodiment of FIG. 5. The difference is that the alternative embodiment has a thin transition zone between elements 50 and 58, between elements 58 and 60, and between elements 60 and 62. These transition zones, noted as 64a, 66a, and 68a, correspond to the junctions 64, 66 and 68 of the embodiment of FIG. 5. These transition zones are fabricated using a combination of the materials at both sides of the transition. For example, a portion of the material of element 50 (e.g., platinum) is combined with a portion of the material of element 58 (e.g., polypyromellitimide) to produce transition zone 64a. These transition zones are relatively small, being less than half of the diameter of the elements 58 and 60.

Transition zones 68a and 66a are similarly created. The electrical effect of these transition zones is to create a set of two junctions of intermediate conductivity rather than the abrupt junction that exists in the embodiment of FIG. 5. It is felt that these transition zones are relatively easy to manufacture using the preferred materials and molding techniques. However, an additional cost is incurred and the embodiment should be employed only when this additional cost is justified by the decreased losses in conductivity through the electrode and decreases in polarization effects at the electrode.

Figure 7:
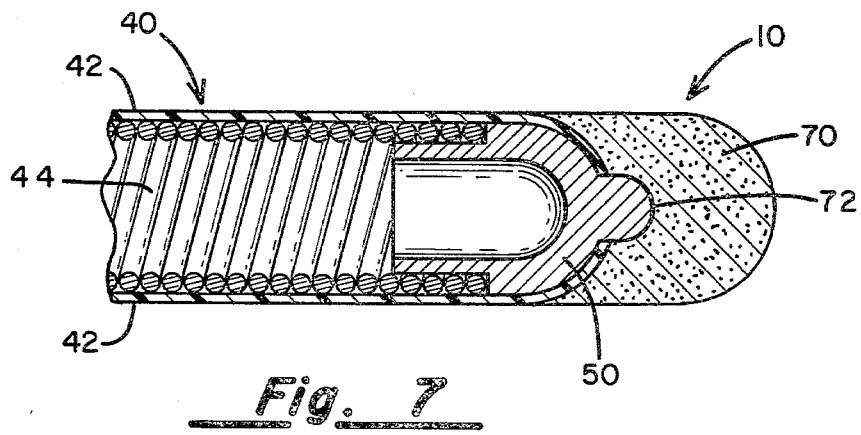
FIG. 7 is a cross-sectional view of a semiconductor electrode having a non-graded structure.

FIG. 7 shows a third embodiment. This embodiment employs a relatively large difference in conductivity between element 50 and element 70. In this case element 50 is again a highly conducting metal, preferably platinum as in the previous examples. However, there is no smooth or gradual transition to element 70 which has a conductivity in the semiconductor range. Element 70 is a semiconductor, preferably having a resistivity in the range of $10^6$ to $10^8$ microhm cm. A material suitable for this purpose would be cross-linked polyacrylamide. Again, as with the previous embodiments, it is also important that element 70 be of a material which is fully biocompatible. The junction established between element 50 and element 70 is junction 72. Again, because of the construction of this particular embodiment, the junction 72 represents a substantial change in conductivity.

The embodiment taught in the FIG. 7 is desirable because there are fewer materials involved and fewer manufacturing steps. This embodiment should be used for systems wherein a natural stimulation threshhold sufficiently high as to absorb the losses inherent in junction 72 and wherein the material selected for element 70 may be of relatively low resistivity. By relatively low resistivity we mean in the range $10^5$ to $10^8$ microhm cm. Notice that this would correspond to stimulatable body tissue having a lower natural impedance than that found in the previous two embodiments.

Having thus described three embodiments of the present invention it should become apparent to the reader that quite a number of different mechanical configurations and different materials are possible. Of most importance, however, is that the materials chosen are biocompatible and that the material directly in contact with the body tissue to be stimulated have a characteristic impedance approximating that of the body tissue. As explained above, this provides a relatively good impedance match guaranteeing that the overall energy threshholds of the system have been minimized.

What is claimed is:

1. A body implantable lead comprising:
    a conductor having a proximal end and a distal end;
    a sheath of body compatible material covering said conductor;
    an electrical connector coupled to said proximal end of said conductor; and
    an electrode coupled to said distal end of said conductor, comprising:
    a metallic element of a metallic material coupled to said conductor;
    a first intermediate element of a material having a resistivity greater than the resistivity of the material of said metallic element and less than $10^5$ microhm cm, covering said metallic element; and
    a distal element of body compatible material which is a semiconductor and has a resistivity in the range of $10^5$ to $10^{10}$ microhm cm, covering said intermediate element.

2. A body implantable lead according to claim 1 wherein said distal element is cross-linked polyacrylamide.

3. A body implantable lead according to claim 1 wherein said distal element is polypyrene.

4. A body implantable lead according to claim 1 or claim 2 or claim 3 wherein said electrode further comprises:
    a second intermediate element of a material having a resistivity greater than first intermediate element and less than said distal element electrically coupled between said first intermediate element and said distal element.

5. A body implantable lead according to claim 4 wherein said metallic element is platinum.

6. A body implantable lead according to claim 5 wherein said first intermediate element is polypyromellitimide.

7. A body implantable lead according to claim 4 wherein said electrode further comprises:
    a first transition element between said metallic element and said first intermediate element, of a material having a resistivity greater than the resistivity of said metallic element and less than the resistivity of said first intermediate element;
    a second transition element between said first intermediate element and said second intermediate element, of a material having a resistivity greater than the resistivity of said first intermediate element and less than the resistivity of said second intermediate element; and
    a third transition element between said second intermediate element and said distal element, of a material having a resistivity greater than the resistivity of said second intermediate element and less than the resistivity of said distal element.

8. A body implantable lead according to claim 7 wherein the material of said first transition element is a combination of the material of said metallic element and the material of said first intermediate element, and wherein the material of said second transition element is a combination of the material of said first intermediate element and the material of said second intermediate element, and wherein the material of said third transition element is a combination of the material of said second intermediate element and the material of said distal element.

9. A body implantable lead according to claim 1 wherein said electrode further comprises:
    a first transition element between said metallic element and said first intermediate element, of a material having a resistivity greater than said metallic element and less than said first intermediate element; and
    a second transition element between said first intermediate element and said distal element, of a material having a resistivity greater than the resistivity of said first intermediate element and less than the resistivity of said distal element.

10. A body implantable lead according to claim 9 wherein the material of said first transition element is a combination of the material of said metallic element and the material of said first intermediate element, and wherein the material of said second transition element is a combination of the material of said first intermediate element and the material of said distal element.

* * * * *